(12) United States Patent
Yasutake et al.

(10) Patent No.: US 6,797,496 B1
(45) Date of Patent: Sep. 28, 2004

(54) PROCESS FOR PRODUCING GLYCOSIDES

(75) Inventors: Nozomu Yasutake, Tsukuba (JP);
Shinsuke Miyoshi, Tsukuba (JP);
Taiichi Usui, Shizuoka (JP); Takeomi Murata, Shizuoka (JP); Kazuhide Totani, Shizuoka (JP)

(73) Assignee: Showa Sangyo Co., Ltd. (JP)

( * ) Notice: Subject to any disclaimer, the term of this patent is extended or adjusted under 35 U.S.C. 154(b) by 259 days.

(21) Appl. No.: 10/049,964

(22) PCT Filed: Aug. 18, 2000

(86) PCT No.: PCT/JP00/05576

§ 371 (c)(1),
(2), (4) Date: Jul. 18, 2002

(87) PCT Pub. No.: WO01/14575

PCT Pub. Date: Mar. 1, 2001

(30) Foreign Application Priority Data

Aug. 19, 1999 (JP) .......................................... 11-233262

(51) Int. Cl.[7] .......................... C12P 19/44; C07H 15/04
(52) U.S. Cl. ............................. 435/74; 435/72; 536/4.1
(58) Field of Search ............................. 435/74, 72, 84, 435/99; 536/4.1

(56) References Cited

U.S. PATENT DOCUMENTS

| 5,149,640 A | 9/1992 | Oonishi et al. |
| 5,153,128 A | 10/1992 | Nakayama et al. |

FOREIGN PATENT DOCUMENTS

| JP | (1982) 59-82096 | 10/1982 |
| JP | (1990) 2-69192 A | 3/1990 |
| JP | (1990) 2-242692 A | 9/1990 |
| JP | (1991) 3-035787 A | 2/1991 |
| JP | (1991) 3-277276 A | 12/1991 |
| JP | (1993) 5-64594 A | 3/1993 |
| JP | (1998) 10-245402 A | 3/1997 |
| JP | (1998) 10-33194 A | 2/1998 |
| JP | (1998) 10-66595 A | 3/1998 |

OTHER PUBLICATIONS

Joziasse, David H. et al.: "α1 → 3–Galactosyltransferase: the use of recombinant enzyme for the synthesis of α–galactosylated glycoconjugates", *Eur. J. Biochem.* 191, 75–83(1990), pp. 75–83.

Trimble, Robert B. et al., "Transfer of Glycerol by Engo–β–N–acetylglucosaminidase F to Oligosaccharides during Chitobiose Core Cleavage". *The Journal of Biological Chemistry*, vol. 261, No. 26, Sep. 15, 1986, pp. 12000–12005.

(List continued on next page.)

*Primary Examiner*—Francisco C Prats
(74) *Attorney, Agent, or Firm*—Webb Ziesenheim Logsdon Orkin & Hanson, P.C.

(57) ABSTRACT

A lactosyl glycoside or an N-acetyllactosaminyl glycoside useful as foods, functional food materials, medicines, and reagents is provided with high yield and inexpensively by using a transfer reaction represented by the following formula in the presence of an enzyme having an activity of cleaving a β1,4 glucosyl bond:

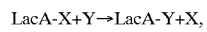

wherein LacA represents lactose or N-acetyllactosaminide; X represents hydrogen (H), a saccharide, a glycoconjugate, or a phenolic compound; and Y represents a compound having an alcoholic hydroxyl group or a phenolic hydroxyl group.

17 Claims, 5 Drawing Sheets

OTHER PUBLICATIONS

Bardales, Richard M. et al., "Transglycosylation and Transfer Reaction Activities of Endo-α-N-acetyl-D-galactosaminidase from Diplococcus (Streptococcus)". *The Journal of Biological Chemistry*, vol. 264, No. 33, Nov. 25, 1989, pp. 19893–19897.

Yamamoto, Kenji et al., "Transglycosylation Activity Of *Mucor hiemalis* Endo-β-N-Acetylglucosaminidase Which Transfers Complex Oligosaccharides to the N-Acetylglucosamine Moieties of Peptides", *Biochemical and Biophysical Research Communications*, vol. 203, No. 1, Aug. 30, 1994, pp. 244–252.

Takenaka, Fumihito et al., "Synthesis of α-D-Glucosylglycerol by α-Glucosidase and Some of Its Characteristics", *Biosci. Biotechnol. Biochem.*, 64 (9), 2000, pp. 1821–1826.

Nakano, Hirofumi et al., "Transfer Reaction Catalyzed by Exo-α-1,4-galactanase from *Bacillus subtilis*". *Agric. Biol. Chem.*, 55 (8), 1991, pp. 2075–2082.

Hronowski, Lucjan J.J. et al., "Synthesis and characterization of 2-O-β-lactosylglycerol. 1,2-di-O-β-lactosyl-(R, S)-glycerols, and 1,2,3-tri-O-β-lactosylglycerol", *Carbohydrate Research*, 219 (1991), pp. 33–49, Elsevier Science Publishers B.V., Amsterdam.

PROCESS FOR PRODUCING GLYCOSIDES

BACKGROUND OF THE INVENTION

1. Field of the Invention

The present invention relates to a method for producing lactosyl glycosides or N-acetyllactosaminyl glycosides. More specifically, the present invention relates to a method for producing lactosyl glycosides or N-acetyllactosaminyl glycosides, using an enzyme having an activity of cleaving a β-1,4 glucosyl bond.

2. Description of the Prior Art

Oligosaccharides and glycoconjugates (glycoproteins, glycolipids, glycosides, etc.) are present in animals and plants, for example, biological cells, body fluids, fruits, seeds, etc. These components have essential functions to maintain or regulate biological functions such as the transmission of biological information on the surface of a cell membrane, the morphogenesis of cells, the maintenance of a specific structure that is composed of covalent bonds with proteins, just like genes and proteins.

Glycolipids, certain kinds of glycoconjugates, are classified into sphingoglycolipids, glycoglycerolipids and others. Sphingoglycolipids are present mostly in animal tissues, and are classified roughly into four series, namely the globo-, the lacto, the ganglion, and the gala-series, depending on their basic sugar chain component. Three of those series, the globo-, the lacto-, and the ganglio-series, have a lactose unit and lactosylceramide unit in which lactose is bound to ceramide as the basic backbone, and are classified depending on the saccharide to be added next.

Lactosylceramide has a Galβ1–4Glc unit, that is, a lactose unit. It has come to be known that bacteria recognize this lactose unit to recognize the sequence of a glycoconjugate. The mechanism that a microorganism adheres to a host cell via a sugar chain plays an important role as a model of inter-cell recognition. Furthermore, it has come to be known that bacteria not only recognize the end of a sugar chain on the surface of a cell for binding, but also recognize the sugar chain structure inside the sugar chain. For example, it is known that *E. coli*, microorganisms belonging to genus Pseudomonas, Actinomycetes, and propionibacteria recognize the lactose unit that is present inside of various sugar chains as well.

Thus, lactosylceramide as described above plays a physiologically important role in such as adhesion of cells. Therefore, lactosyl glycoside can be used for the applications of medicine, food and the like, but it is not easy to produce the lactosyl glycoside at present.

There are many kinds of glycosides as glycoconjugates. For example, the glycosides which are composed of sugar unit (glucose, galactose and N-acetyllactosaminide), and glycerol as the aglycon, are known. Naturally occurring components such as glyceroyl glucoside (2-O-α-D-Glucosylglycerol, (2R)-1-O-α-D-Glucosylglycerol, and (2S)-1-O-α-D-Glucosylglycerol) are known as the glycoside for glucose. Glyceroyl galactoside (1-O-β-D-Galactosylglycerol) as a chemically synthesized substance is known as the glycoside for galactose. As the glycoside for N-acetyllactosaminide, the existence of O-β-D-Galactopyranosyl-(1→4)-O-β-D-2-Acetyl-amino-2-deoxyl-Glucopyranosyl-(1→2)-Gycerol is reported.

Among the abovedescribed glycosides, glyceroyl glucoside, glyceroyl galactoside and the like are characterized by their taste, their moisture retaining properties, and their physiological functions. These substances are also useful as a starting material for the synthesis of glycoglycerolipids. Glycoglycerolipids are present widely in organisms, ranging from microorganisms to higher plants, and are reported to have emulsification stability and carcinogenic promoter suppressing effects. Therefore, compounds in which saccharides having different structures are added to glycerol can be expected to have new functions or to be applied as new starting materials of glycoglycerolipids.

N-Acetyllactosaminyl glycosides are known to be present in a receptor recognized by Staphylococcus or the core unit of the sugar chain structure recognized by influenza viruses A and B, Sendai virus, Newcastle disease virus and the like, and participate in the recognition of cells. Therefore, the N-acetyllactosaminyl glycosides are useful for medical applications, but it is not easy to produce N-acetyllactosaminyl glycosides at present.

The functions of such saccharide-related substances are noted, therefore, modification and substitution research (remodeling) of sugar chains and glycoconjugates is performed in order to utilize the substances for medical and food applications by improving these functions further or modifying their physiological functions.

For remodeling the sugar chains of saccharides and glycoconjugates, there are chemical methods, enzymatic methods, and methods combining chemical and enzymatic methods.

As a chemical method, there is an organic synthesis method for sugar chain synthesis, but this method involves many complicated steps, and a process for removing byproducts (purifying a desired substance) is necessary. Furthermore, reagents that are harmful to human health are often used, and there is the fear that the waste liquid may damage the surrounding environment.

On the other hand, for remodeling sugar chains enzymatically, a method using transferase, exoglucosidase, endoglucosidase, and the like are known.

One of the methods using transferase or exoglucosidase is described in D. H. Joziasse et al. Eur. J. Biochem., vol. 191, pages 75–83 (1990), which discloses a method of sequentially adding a glucosyl group to a nonreducing end of a sugar chain by using exoglucosidase or glucosyltransferase.

However, although the sugar chain synthesis using exoglucosidase or glucosyltransferase is easier than chemical synthesis, it is still necessary to perform an enzyme reaction sequentially for each saccharide residue one by one, so that a large number of reaction steps are required, which makes the method troublesome.

Examples of the disclosure of transglycosylation using endoglucosidase are as follows. R. B. Trimble et al. J. Biol. Chem., vol. 261, pp. 12000–12005 (1986) describe a method of using endo-β-N-acetylglucosaminidase derived from *Flavobacterium meningosepticum*. R. M. Bardales et al., J. Biol. Chem., vol. 264, pp. 19893–19897 (1989) describe a method of using endo-α-N-acetylgalactosaminidase derived from *Diprococcus pneumoniae*. Japanese Laid-Open Patent Publication (Tokkai) No. 5-64594 describes a transfer reaction of high-mannose type of sugar chains to saccharides by using endo-β-N-acetylglucosaminidase derived from *Arthrobacter protophormiae*. K. Yamamoto et al., Biochem. Biophys. Res. Commun., vol. 203, pp. 244–252 (1994) describe a transfer reaction of a sugar chain to a saccharide by using endo-β-acetylglucosaminidase derived from *Mucor hiemalis*. Japanese Laid-Open Patent Publication (Tokkai) No. 10-245402 describes a transfer reaction of (Man)$_6$-GlcNAc using endo-β-N-acetylglucosaminidase. Japanese Laid-Open Patent Publication (Tokkai) No. 10-33194 describes a transfer reaction of Galβ1–3GlcNAc using lacto-N-biosidase.

As described above, examples of transferring various sugar chains by using endoglucosidases have been reported, but there has been no example of transferring lactose or N-acetyllactosaminide unit so far.

Therefore, there is a need for a method for producing lactosyl glycosides or N-acetyllactosaminyl glycosides in a simple manner.

SUMMARY OF THE INVENTION

The present invention is directed to a method for producing a lactosyl glycoside or an N-acetyllactosaminyl glycoside comprising using a transfer reaction represented by the following formula in the presence of an enzyme having an activity of cleaving a β1,4 glucosyl bond:

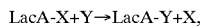

LacA-X+Y→LacA-Y+X, wherein LacA represents lactose or N-acetyllactosaminide; X represents hydrogen (H), a saccharide, a glycoconjugate, or a phenolic compound; and Y represents a compound having an alcoholic hydroxyl group or a phenolic hydroxyl group.

In one preferable embodiment, Y is a compound having an alcoholic hydroxyl group.

In another preferable embodiment, the compound having an alcoholic hydroxyl group is an aliphatic alcohol or a saccharide.

In yet another preferable embodiment, the compound having an alcoholic hydroxyl group is an amino acid, a peptide or a protein having a serine or threonine residue.

In one preferable embodiment, X is hydrogen.

In one preferable embodiment, the enzyme having an activity of cleaving a β-1,4 glucosyl bond is exo-cellobiohydrolase, β-D-glucosidase, and/or cellulase.

The present invention is also directed to glyceroyl N-acetyllactosaminide (O-β-D-Galactopyranosyl-(1→4)-O-β-D-2-Acetyl-amino-2-deoxyl-Glucopyranosyl-(1→1)-Glycerol) represented by the structural formula (I):

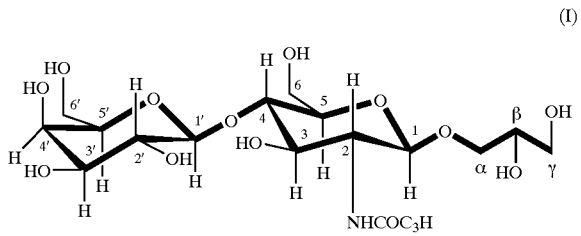

(I)

DETAILED DESCRIPTION OF THE INVENTION

Figure 1:
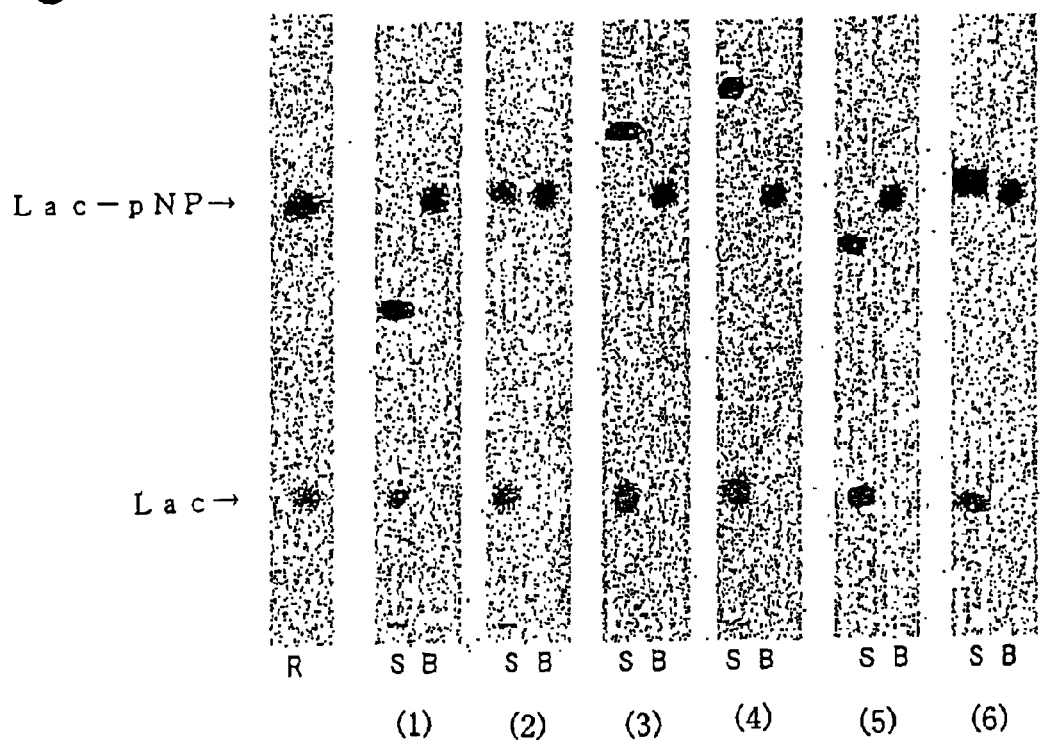
FIG. 1 is the results of thin layer chromatography showing a transfer reaction of the lactosyl group of Lac-pNP to an aliphatic alcohol.

The present invention is directed to a method for producing a lactosyl glycoside or an N-acetyllactosaminyl glycoside characterized by using a transfer reaction represented by the following formula in the presence of an enzyme having an activity of cleaving a β1,4 glucosyl bond:

LacA-X+Y→LacA-Y+X

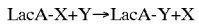

(Enzyme)

There is no limitation regarding the enzymes used in the present invention, as long as they have an activity of cleaving a β1,4 glucosyl bond. Either endo-type or exo-type emzyme can be used. Preferable examples of the enzymes include exo-cellobiohydrolase, β-D-glucosidase, and cellulase. These enzymes can be used alone or in combination.

Commercially available enzymes having an activity of cleaving a β1,4 glucosyl bond can be also used in the present invention. Microorganisms that produce the enzymes having an activity of cleaving a β1,4 glucosyl bond, culture medium or extracts thereof, or purified products can be used in the present invention. Microorganisms that produce the enzymes having an activity of cleaving a β1,4 glucosyl bond are known.

Examples of bacteria include microorganisms belonging to genus Bacillus, Cellvibrio, Cellulomonas, Pseudomonas, Sporocytophaga, Acetivibrio, Clostridium, Bacterioides, Treponema, and Ruminococcus.

Examples of filamentous fungi include fungi belonging to genus Humicola, Tricoderma, Myrothecium, Aspergillus, Irpex, Penicillium, and Pellicularia.

Examples of actinomyces include microorganisms belonging to genus Streptomyces, and Thermonospola.

(Donor)

Examples of the lactose or N-acetyllactosaminide donor represented by the formula LacA-X include lactose or N-acetyllactosaminide (when X is hydrogen), and saccharides, glycoconjugates or phenolic compounds containing lactose or N-acetyllactosaminide.

Examples of the saccharides as the lactose donor and/or the N-acetyllactosaminide donor include oligosaccharides containing lactose or N-acetyllactosaminide connected with a β-glucoside linkage.

Examples of the glycoconjugates as the lactose donor and/or the N-acetyllactosaminide donor include glycoproteins, proteoglycans, and glycolipids having lactose or N-acetyllactosaminide at their end. As the glycolipids, sphingoglycolipids are preferable, and one having lactose or N-acetyllactosaminide at the end of a ceramide, which is a component of sphingoglycolipid, or an analogue of the ceramide is preferably used.

There is no particular limitation regarding the phenolic compounds as the lactose or N-acetyllactosaminide donor.

Examples thereof include phenol and its derivatives (e.g., para-nitrophenol), tyrosine and its derivatives, salicylic acid and its derivatives having lactose or N-acetyllactosaminide. When LacA-X is lactose or N-acetyllactosaminide, a condensation reaction occurs between LacA-X and an acceptor Y, and this reaction also is included in the transfer reaction referred to in the present invention.

(Acceptor)

Compounds having a hydroxyl group, that is, an alcoholic hydroxyl group or a phenolic hydroxyl group can be used as Y, which is the acceptor of lactose or N-acetyllactosaminide.

Examples of the compounds having an alcoholic hydroxyl group as the acceptor of lactose or N-acetyllactosaminide include aliphatic alcohols, amino acids, and saccharides.

Aliphatic alcohols have a structure of aliphatic hydrocarbon in which one or more hydrogen atom(s) is substituted with a hydroxyl group, and can be classified into primary alcohols, secondary alcohols, and tertiary alcohols, depending on the number of alkyl groups binding to a carbon atom bound to the hydroxyl group. They can be classified into monohydric alcohols, dihydric alcohols and polyhydric alcohols, depending on the number of binding of hydroxyl group.

Examples of primary alcohols include methanol ethanol, butanol, propanol, hexanol (cis-3-hexanol), octanol, allyl alcohol, geraniol, and citronellol.

Examples of secondary alcohols include isopropanol, and sec-butanol.

Examples of tertiary alcohols include t-butylalcohol.

A typical example of a monohydric alcohol is methanol, a typical example of a dihydric alcohol is ethylene glycol, and a typical example of a trihydric alcohol is glycerol.

In addition to the above-described substances, alicyclic alcohols having a ring structure such as menthol and santalol are included in the aliphatic alcohols.

Examples of the amino acids having an alcoholic hydroxyl group include serine and threonine. Furthermore, peptides and proteins containing the residue of an amino acid having an alcoholic hydroxyl group such as serine and threonine, or peptides containing tyrosine having a phenolic hydroxyl group as described later can be also used as the acceptor of the present invention.

Examples of the saccharides having an alcoholic hydroxyl group include monosaccharides such as glucose and mannose. Examples of the oligosaccharides include: starch-related oligosaccharides such as maltooligosaccharides, isomaltooligosaccharides, cyclodextrin, gentiooligosaccharides and nigerooligosaccharides; sugar-related oligosaccharides such as maltooligosylsucroses, fructooligosaccharides, paratinose, lactosucrose, xylosylfructoside, raffinose and stachyose; lactose-related oligosaccharides such as galactooligosaccharides, lactosucrose and lactulose; xylooligosaccharides; agarooligosaccharides; chitin/chitosan oligosaccharides; mannooligosaccharides; and alginate oligosaccharides. Furthermore, a sugar chain that is a component of a glycoprotein or a glycolipid, or a sugar chain that is a partial structure thereof can be used.

Examples of the compounds having a phenolic hydroxyl group include phenol and its derivatives, tyrosine and its derivatives, salicylic acids and their derivatives, and soybean isoflavones such as genistein.

In addition, glycoconjugates such as glycoproteins and sphingoglycolipids, conjugated lipids such as ceramide, flavonoid analogues such as flavonol have a hydroxyl group, and can be used as the acceptor.

(Lactosyl or N-acetyllactosnyl Transfer Reaction)

There is no particular limitation regarding the lactosyl or N-acetyllactosaminyl transfer reaction. It is sufficient to mix a lactosyl or N-acetyllactosaminyl donor, an enzyme having an activity of cleaving a β-1,4 glucosyl bond, and a lactosyl or N-acetyllactosaminyl acceptor in an appropriate ratio to allow to react.

There is no particular limitation regarding the concentrations of the lactosyl or N-acetyllactosaminyl donor and acceptor in the transfer reaction, and the concentrations can be determined as appropriate by those skilled in the art, in view of the efficiency of the reaction or the like.

There is no particular limitation regarding the concentration of the enzyme used, and the concentration can be determined as appropriate by those skilled in the art, in view of the concentration of the substrate, the reaction temperature, the reaction time or the like. For example, the amount of the enzyme to be used can be determined by performing a preliminary test.

There is no particular limitation regarding the reaction temperature. In general, the reaction temperature is in the range of about ±20° C. of the optimum temperature of the enzyme used. More preferably, it is in the range of about ±10° C. of the optimum temperature of the enzyme.

There is no particular limitation regarding the pH for the reaction. Although it depends on the enzyme used, in general, the reaction is performed in the range of about ±3 of the optimum pH of the enzyme used, more preferably about ±2 of the optimum pH of the enzyme. For pH adjustment to such a value, a suitable buffer routinely used by those skilled in the art can be used.

When it is difficult to dissolve the substrate in water, a small amount of a solvent or a surfactant can be added to water to dissolve the substrate to increase the reaction efficiency.

EXAMPLES

Hereinafter, the present invention will be described by way of examples, but the present invention is not limited thereto.

Example 1

A lactosyl transfer reaction was performed by using aliphatic alcohols as the acceptor. As the lactose donor, p-nitrophenyl-β-D-lactoside (hereinafter, referred to as "Lac-pNP") was used, and ethanol, butanol, hexanol, octanol, isopropanol, and t-butylalcohol, which are aliphatic alcohols, were used as the lactose acceptor. As the enzyme, cellulase (manufactured by Kyowa Hakko Kogyo Co., Ltd.) derived from *Trichoderma reesei* was used.

First, 200 μl of 4.65 mg/ml of Lac-pNP, 120 μl of one of the alcohols, and 30 μl of 0.2M acetate buffer (pH 5.5) were added to 50 μl of 10 mg/ml of an enzyme solution (dissolved in 20 mM acetate buffer (pH 5.0)) so that the total volume was 400 μl. An enzyme reaction was performed at 40° C., and a transfer reaction was monitored over time by thin layer chromatography (hereinafter, referred to as "TLC": with chloroform:methanol:water=60:35:8 as the developing solvent). Aluminum Sheet Silicagel 60/Kieselgur F254 Precoat manufactured by Merck was used for the TLC. Detection was performed by color-development with orcine-sulfuric acid method.

The results are shown in FIG. 1. In FIG. 1, R shows a mixture of lactose (Lac) and Lac-pNP, and the Rf value (0.13) of the lactose is smaller than that (0.43) of Lac-pNP. S refers to a reaction mixture, and B refers to a blank. The blank was obtained by adding water instead of the enzyme for reaction. In FIG. 1, (1), (2), (3), (4), (5) and (6) show the results when ethanol, butanol, hexanol, octanol, isopropanol, and t-butylalcohol, respectively, were used as the substrate.

Lactose (Lac) that had not been present in an early stage of the reaction was produced in all the reaction mixtures S of (1) to (6), and alkyl lactoside corresponding to each substrate of (1) to (6) (ethyl lactoside, butyl lactoside, hexyl lactoside, octyl lactoside, isopropyl lactoside, and t-butyl lactoside, respectively) was further produced. In other words, it was confirmed that in all of the reaction mixtures of (1) to (6), the lactosyl group of Lac-pNP was transferred to the hydroxyl group of the aliphatic alcohol, so that the alkyl lactoside was produced. The Rf value (0.38) of the butyl lactoside of (2) and the Rf value (0.45) of the t-butyl lactoside of (6) were close to the Rf value (0.43) of Lac-pNP, so that in the TLC of FIG. 1, (2) and (6) were difficult to distinguish from Lac-pNP visually.

Example 2

The reaction product ((1)) obtained using ethanol as the lactose acceptor of Example 1 was analyzed. A reaction was performed for 27 hours, and the reaction product was heated at 100° C. for 10 minutes, and centrifuged at 17,000 rpm for 10 minutes to give a supernatant. The supernatant was evaporated to dryness, and then dissolved in 10 ml of 25% aqueous methanol. The solution was loaded to Toyopearl HW-40S gel filtration column ($\phi$2.5×80 cm), and fractionated into 10 ml fractions with a 25% aqueous methanol as the eluent at a flow rate of 1.0 ml per min. The fractions were detected by measuring the UV absorption at 210 nm and 300 nm and the color-development (485 nm) by the phenol-sulfuric acid method. The fractions of tube Nos. 34 to 44 were pooled and evaporated to dryness.

The dried product was dissolved in 10 ml of chloroform:methanol:water=50:45:10 to separate and purify by silica gel column chromatography using Wakogel C-300. Elution was performed at a flow rate of 2.0 ml/min with chloroform:methanol:water=50:45:10 as the developing solvent, and the eluate was fractionated into 10 ml fractions. The fractions were detected by measuring the UV absorption at 210 nm and 300 nm and the color-development (485 nm) by the phenol-sulfuric acid method. The fractions of tube Nos. 11 to 13 were pooled and evaporated to dryness.

Figure 2:
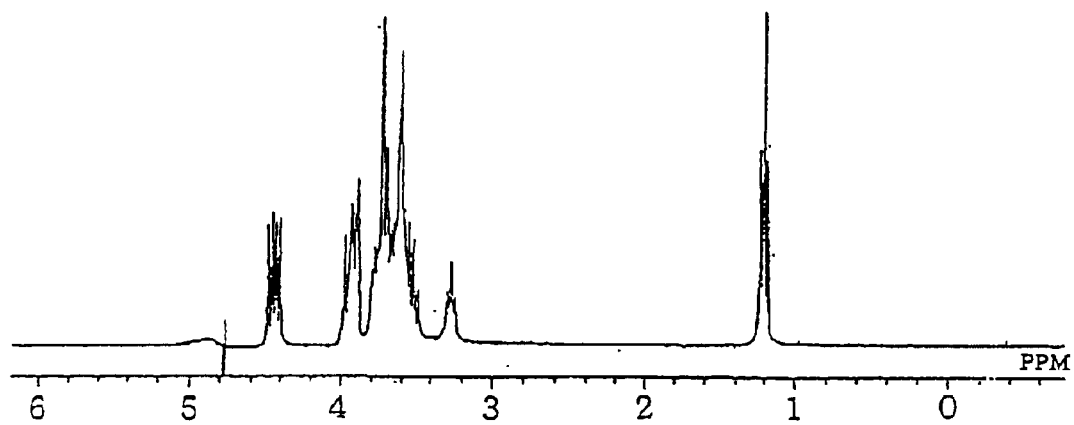
FIG. 2 is a $^1$H-NMR analysis of ethyl lactoside.
Figure 3:
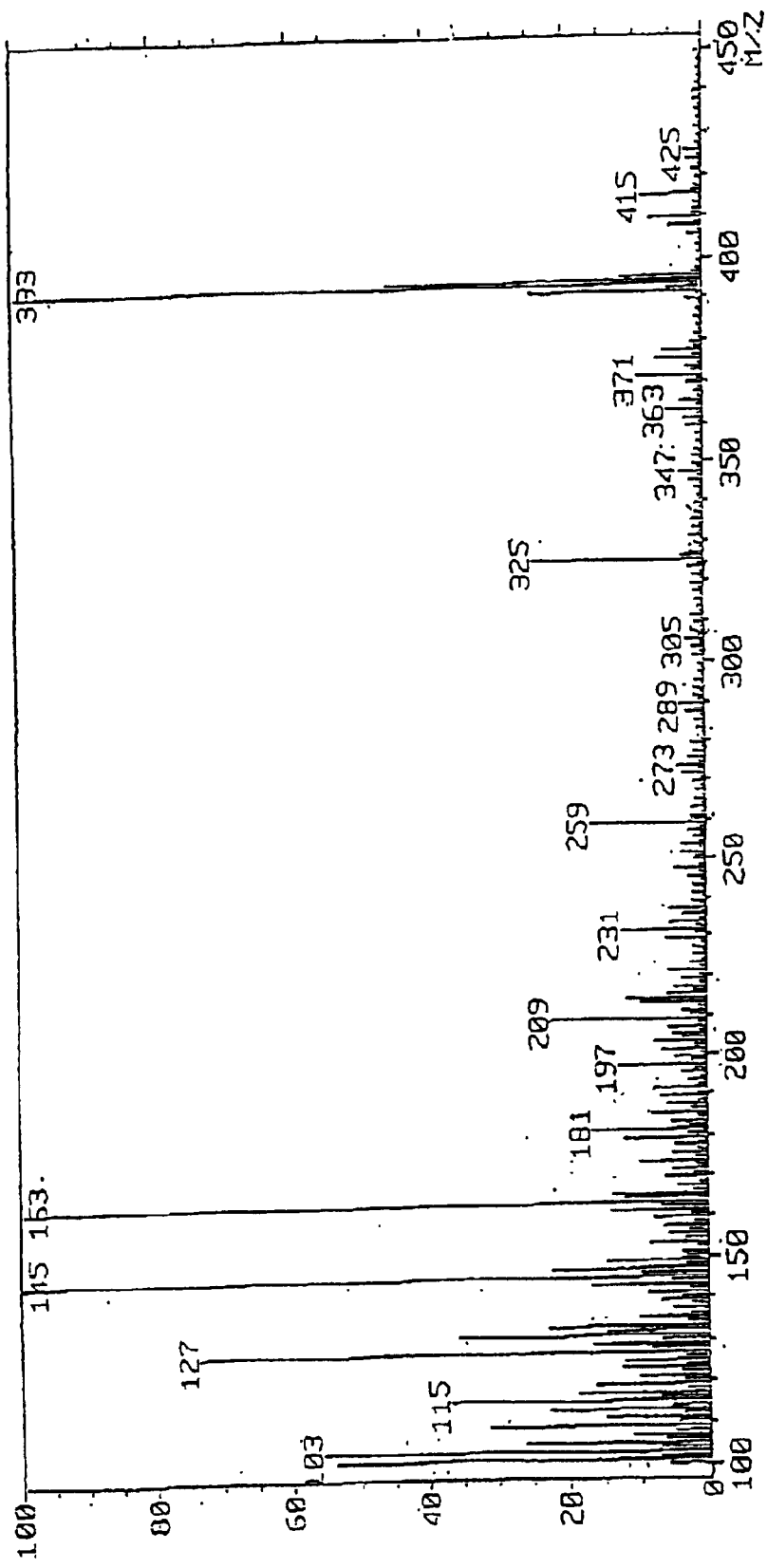
FIG. 3 is a mass spectrum analysis of ethyl lactoside.

A portion of the obtained dried product was dissolved in 0.3 ml of distilled water and subjected to mass analysis FAB/MAS. On the other hand, a portion of the obtained dried product was dissolved in heavy water and subjected to $^1$H-NMR analysis. The result of the $^1$H-NMR is shown in FIG. 2, and the result of the FAB/MAS is shown in FIG. 3. The data of the $^1$H-NMR and the FAB/MAS corresponding to FIGS. 2 and 3 are shown below.

$^1$H-NMR (270 MHz, D$_2$O): $\delta$ 4.50 (d, J 7.9 Hz, H-1), 4.45 (d, J 7.7 Hz, H-1'), 3.30 (dd, H-2), 1.24 (t, H-$\beta$);

FAB/MAS: (m/z)=371 (C$_{14}$H$_{26}$NO$_{11}$+H)$^+$, (m/z)=393 (C$_{14}$H$_{26}$NO$_{11}$+Na)$^+$.

These data confirmed that the product of (1) was ethyl lactoside represented by the structural formula (II):

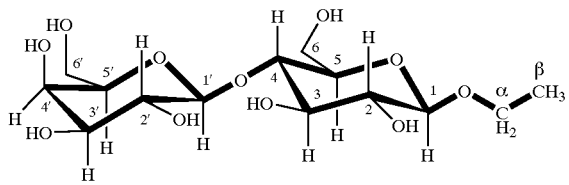

(II)

Example 3

Figure 4:
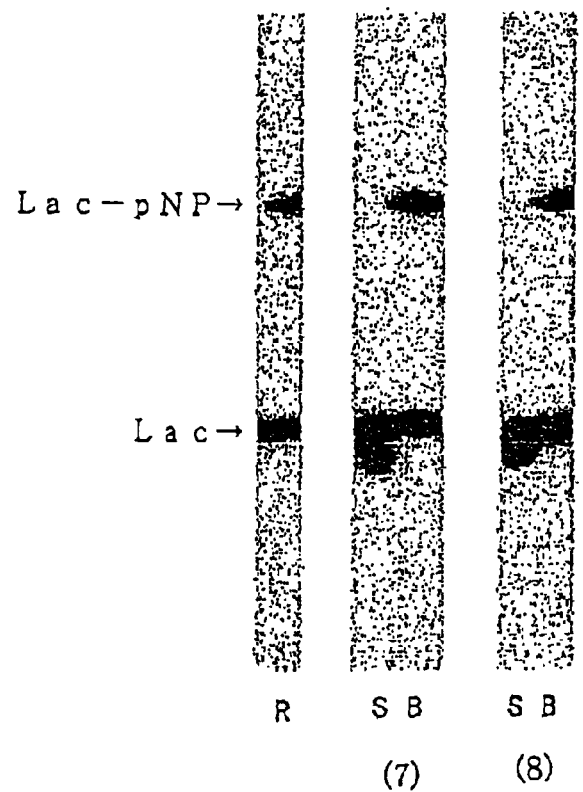
FIG. 4 is the results of thin layer chromatography showing a transfer reaction of the lactosyl group of Lac-pNP to an amino acid.

A lactosyl transfer reaction to an amino acid having an alcoholic hydroxyl group was performed. The same enzyme and lactose donor as that in Example 1 were used. As a reaction mixture, 400 $\mu$l of 15 mM acetate buffer (pH 5.0) containing 0.5 mg of the enzyme, 0.94 mg of Lac-pNP, and 50 mg of serine or 15 mg of threonine were prepared, and allowed to react at 40° C. for 24 hours. After the reaction, analysis was performed by TLC in the same manner as in Example 1. The results are shown in FIG. 4. The developing solvent was chloroform:methanol:water=50:45:10.

In FIG. 4, R shows a mixture of Lac and Lac-pNP, S shows a reaction mixture, and B shows a blank. The results when serine was used as the acceptor is shown in (7), and the results when threonine was used as the acceptor is shown in (8). In the reaction mixtures of (7) and (8), the substrate Lac-pNP disappeared and seryl lactoside and threonyl lactoside were produced, respectively. The Rf values of the seryl lactoside and the threonyl lactoside were 0.27 and 0.29, respectively, and were close to the Rf value (0.34) of lactose so that the seryl lactoside and the threonyl lactoside were not distinctly separated from lactose but they appeared as a broad band.

Example 4

Figure 5:
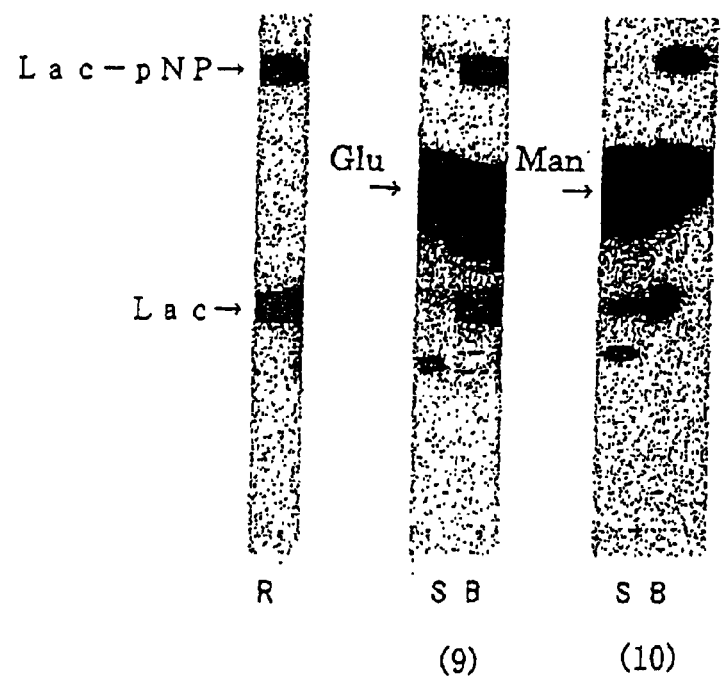
FIG. 5 is the results of thin layer chromatography showing a transfer reaction of the lactosyl group of Lac-pNP to a monosaccharide.

A lactosyl transfer reaction to a monosaccharide having an alcoholic hydroxyl group was performed. The same enzyme and lactose donor as in Example 1 were used. As a reaction mixture, 400 $\mu$l of 15 mM acetate buffer (pH 5.0) containing 0.5 mg of the enzyme, 0.94 mg of Lac-pNP, and 70 mg of glucose or mannose were prepared, and allowed to react at 40° C. for 24 hours. After the reaction, analysis was performed by TLC in the same manner as in Example 1. The results are shown in FIG. 5. The developing solvent was chloroform:methanol:water=50:45:10.

In FIG. 5, R shows a mixture of Lac and Lac-pNP, S shows a reaction mixture, and B shows a blank. The results when glucose was used as the acceptor is shown in (9), and the results when mannose was used as the acceptor is shown in (10). In the reaction mixtures of (9) and (10), the substrate Lac-pNP disappeared and glucosyl lactoside and mannosyl lactoside were produced, respectively. The Rf values of the glucosyl lactoside and the mannosyl lactoside were 0.24 and 0.25, respectively, and were smaller than the Rf value (0.34) of lactose (Lac) so that they were distinctly separated from lactose.

In FIG. 5, there are bands between Lac-pNP and Lac. In (9), the band is glucose (Glu) and in (10), the band is mannose (Man).

Example 5

Figure 6:
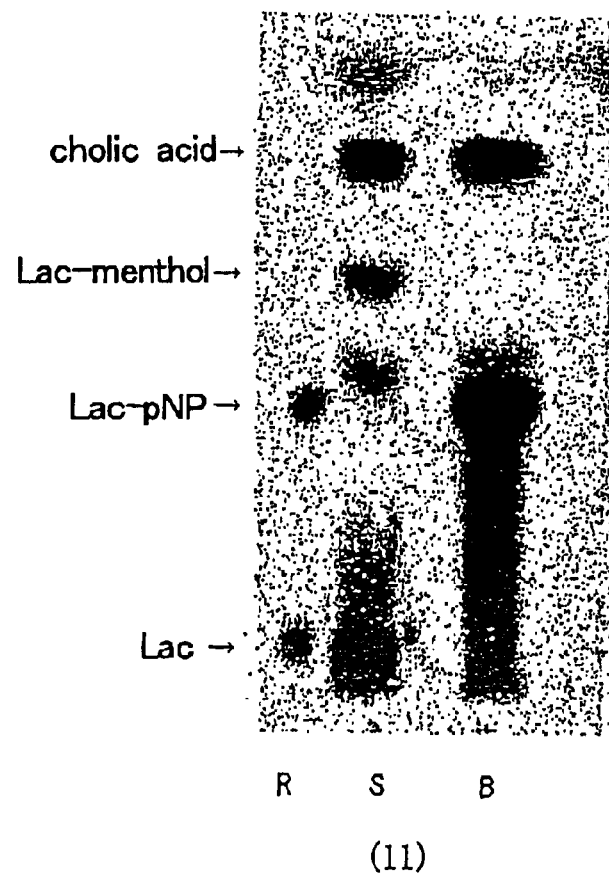
FIG. 6 is the results of thin layer chromatography showing a transfer reaction of the lactosyl group of Lac-pNP to L-menthol.

A lactosyl transfer reaction to L-menthol, which is one of alicyclic alcohols having an alcoholic hydroxyl group, was performed. The same enzyme and lactose donor as that in Example 1 were used. As a reaction mixture, 400 $\mu$l of 15 mM acetate buffer (pH 5.0) containing 1 mg of the enzyme, 1 mg of Lac-pNP, 5 mg of L-menthol, and 2 wt % of cholic acid as a surfactant were prepaered, and allowed to react at 40° C. for 24 hours. After the reaction, analysis was performed by TLC in the same manner as in Example 1. The results are shown in FIG. 6. The developing solvent was chloroform:methanol:water=65:35:4.

In FIG. 6, R shows a mixture of Lac and Lac-pNP, S shows a reaction mixture, and B shows a blank. The substrate Lac-pNP disappeared, and L-mentholyl lactoside (Lac-menthol) was produced (Rf value of 0.62) and was distinguished from lactose (Rf value of 0.13). The spots other than that of L-mentholyl lactoside and the cholic acid having an Rf value of 0.81 seem to indicate some reaction products.

Example 6

An N-acetyllactosaminyl transfer reaction to an aliphatic alcohol having an alcoholic hydroxyl group was performed.

Figure 7:
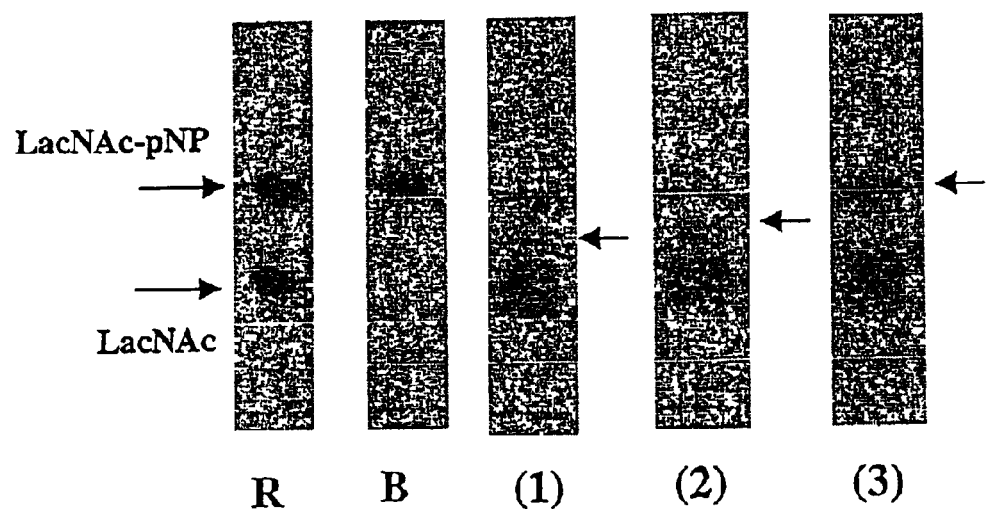
FIG. 7 is the results of thin layer chromatography showing a transfer reaction of the N-acetyllactosaminyl group of LacNAc-pNP to an aliphatic alcohol.

As the N-acetyllactosaminide donor, p-nitrophenyl-β-N-acetyllactosaminide (hereinafter, referred to as "LacNAc-pNP") was used. As a reaction mixture, 400 μl of 15 mM acetate buffer (pH 5.0) containing 0.94 mg of LacNAc-pNP, 120 μl of methanol, ethanol or propanol as the N-acetyflactosaminide (hereinafter, referred to as "LacNAc") acceptor, 0.5 mg of cellulase (manufactured by Kyowa Hakko Co., Ltd.) derived from *Trichoderma reesei* as the enzyme were prepared, and allowed to react at 40° C. for 24 hours. After the reaction, analysis was performed by TLC in the same manner as in Example 1. The results are shown in FIG. 7. The developing solvent was chloroform:methanol:water=50:40:50.

In FIG. 7, R shows LacNAc and LacNAc-pNP, and B shows a blank. The substrate LacNAc-pNP (Rf=0.56) disappeared, and LacNAc (Rf value of 0.30) and new spots indicated by the arrows having Rf values of 0.38, 0.46, and 0.56 appeared, and they were found to correspond to methyl N-acetyflactosaminide (1), ethyl N-acetyllactosaminide (2) and propyl N-acetyllactosaminide (3), respectively. Among them, the spot of the ethyl N-acetyllactosaminide (2) by TLC matched the spot of a specimen (manufactured by Carbiochem).

Example 7

A lactosyl transfer reaction (condensation of lactose) using an aliphatic alcohol and a saccharide having an alcoholic hydroxyl group as an acceptor was performed. As the donor, lactose was used. As the acceptor, methanol, ethanol, propanol, butanol, hexanol, octanol, dodecanol, allyl alcohol, and mannose were used.

Figure 8:
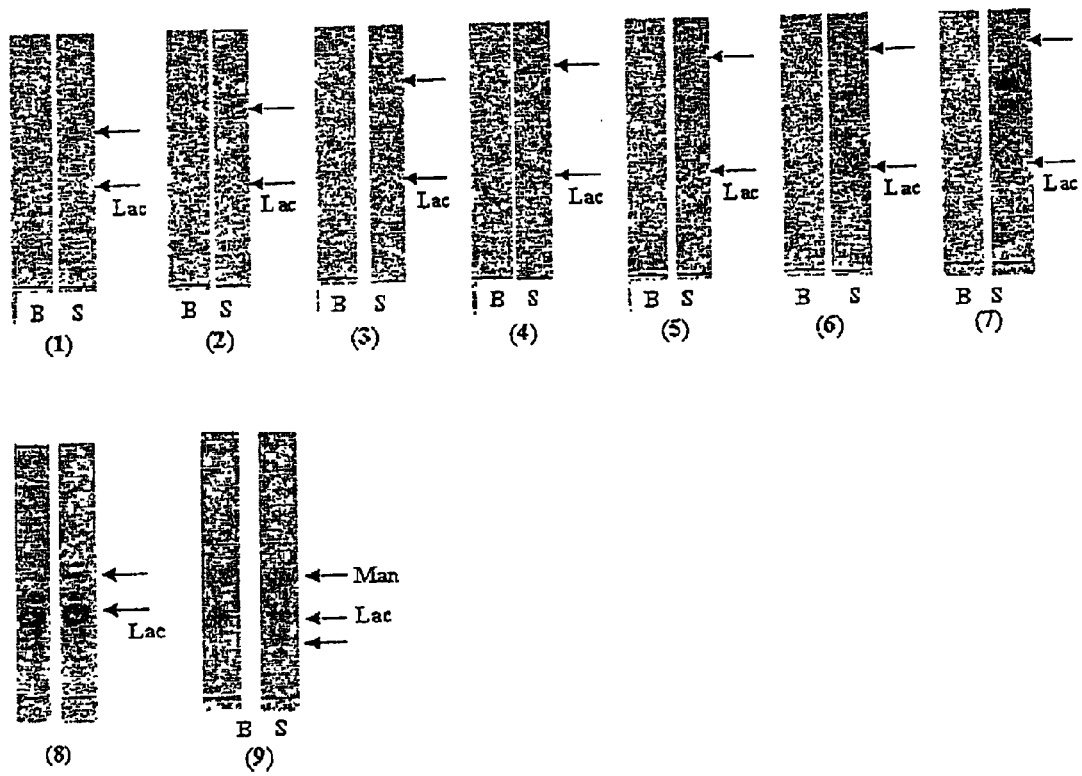
FIG. 8 is the results of thin layer chromatography showing a condensation reaction of lactose and an aliphatic alcohol or a monosaccharide.

First, 650 μl of 10 mM acetate buffer (pH 5.0) containing 100 mg of lactose, 170 μl of one of the acceptors (75 mg in the case of mannose), 25 mg of cellulase (manufactured by Kyowa Hakko Kogyo Co., Ltd.) derived from *Trichoderma reesei* as the enzyme were prepared, and allowed to react at 40° C. for 48 hours. After the reaction, analysis was performed by TLC. The results are shown in FIG. 8 (1) to (7). In FIG. 8, S shows the reaction mixture, and B shows a blank. The developing solvent was chloroform:methanol:water=60:35:8.

In all the reaction mixtures, a plurality of spots that were distinguished from lactose (Lac) having an Rf value of 0.29 were appeared. The new spots are indicated by arrows corresponding to Rf values of 0.45, 0.52, 0.54, 0.62, 0.65, 0.68, and 0.69. These spots suggested that methyl lactoside (1), ethyl lactoside (2), propyl lactoside (3), butyl lactoside (4), hexyl lactoside (5), octyl lactoside (6), and dodecyl lactoside (7) were produced.

With respect to the Rf value of 0.36 of lactose, new spots having Rf values of 0.53 and 0.29 (the developing solvent was chloroform:methanol:water=50:45:10) were seen ((8) and (9) in FIG. 8). These spots suggested that allyl lactoside (8) and mannosyl lactoside (9), respectively, were produced. Each product was confirmed as follows.

7-1 Ethyl Lactoside (2)

The spot of ethyl lactoside (2) by TLC matched that of the transfer reaction product of Lac-pNP and ethanol in Example 1 and a specimen (manufactured by Sigma Corporation). Separation and purification were performed in the same manner as described in Example 2, and a portion of the obtained dried product was analyzed by FAB/MAS, $^1$H-NMR and $^{13}$C-NMR. The results are shown below.

FAB/MAS: (m/z)=371 $(C_{14}H_{26}NO_{11}+H)^+$, (m/z)=393 $(C_{14}H_{26}NO_{11}+Na)^+$;

$^1$H-NMR (270 MHz, $D_2O$): δ 4.50 (d, J 7.9 Hz, H-1), 4.45(d, J 7.7 Hz, H-1'), 3.30 (dd, H-2), 1.24 (t, H-β);

$^{13}$C-NMR (270 MHz, $D_2O$): 17.1 (C-β), 62.9 (C-6), 63.8 (C-6'), 69.0 (C-4'), 71.4 (C-α), 73.8 (C-2'), 75.4 (C-3'), 75.6 (C-2), 77.3 (C-3), 77.6 (C-5), 78.2 (C-5'), 81.3 (C-4), 104.5 (C-1), 105.7 (C-1').

From the above, the product (2) was confirmed to be ethyl lactoside represented by the structural formula (II).

7-2 Butyl Lactoside (4), Hexyl Lactoside (5), Octyl Lactoside (6)

The spots of butyl lactoside (4), hexyl lactoside (5), and octyl lactoside (6) by TLC matched those of the transfer reaction product of Lac-pNP and the corresponding aliphatic alcohols obtained in Example 1.

Furthermore, the reaction mixture that seemed to contain octyl lactoside (6) was applied to the silica gel column (φ2×50 cm) as described above and eluted at a flow rate of 2.0 ml/min with chloroform:methanol:water=60:25:4 as an eluent. The eluate was fractionated into 10 ml fractions and the reaction product was detected by color-development (485 nm) by the phenol-sulfuric acid method. Fractions Nos. 21 to 28 were collected and lyophilized to give about 5 mg of the reaction product. The purity of this product was confirmed to be 99% or more by TLC and liquid chromatography.

A portion of the obtained dried product was analyzed by FAB/MAS and the other portion of the obtained dried product was analyzed by $^1$H-NMR and $^{13}$C-NMR. The results are shown below.

FAB/MAS: (m/z)=455 $(C_{20}H_{38}NO_{11}+H)^+$, (m/z)=477 $(C_{20}H_{38}NO_{11}+Na)^+$;

$^1$H-NMR (270 MHz, $D_2O$): δ 4.48 (d, J 8.0 Hz, H-1), 4.45(d, J 7.7 Hz, H-1'), 3.31 (dd, H-2), 1.63 (m, H-β), 1.36 (m, H-γ), 1.29 (m, H-δ-η), 0.87 (t, H-θ);

$^{13}$C-NMR (270 MHz, $D_2O$): 16.2 (C-θ), 24.8 (C-η), 27.8 (C-γ), 31.2 (C-δ), 31.2 (C-ε), 31.5 (C-β), 33.9 (C-ζ), 63.0 (C-6), 63.8 (C-6'), 71.4 (C-4'), 73.6 (C-α), 73.8 (C-2'), 75.4 (C-3'), 75.7 (C-2), 77.3 (C-3), 77.6 (C-5), 78.2 (C-5'), 81.3 (C-4), 104.8 (C-1), 105.7 (C-1').

From the above, the product (6) was confirmed to be octyl lactoside represented by the structural formula (III):

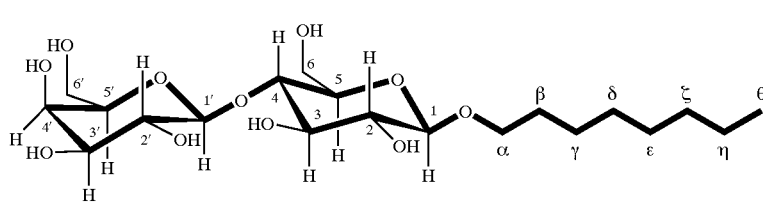

(III)

7-3 Dodecyl Lactoside (7)

The reaction mixture that seemed to contain dodecyl lactoside (7) was applied to ODS column (φ3.5×60 cm) using Chromatorex-ODS DM1020T. The column was washed with 65% methanol in five volume of the column, and then eluted with 75% methanol (a flow rate of 2.5 ml/min). Fractionation was performed at 30 ml/fraction, and the reaction product was detected by color-development (485 nm) by the phenol-sulfuric acid method. Fractions Nos. 17 to 23 were collected and lyophilized to give about 5 mg of the reaction product. The purity of this product was confirmed to be 99% or more by TLC and liquid chromatography.

A portion of the obtained dried product was analyzed by FAB/MAS and the other portion of the obtained dried product was analyzed by $^1$H-NMR and $^{13}$C-NMR. The results are shown below.

FAB/MAS: (m/z)=511 $(C_{24}H_{46}NO_{11}+H)^+$, (m/z)=533 $(C_{24}H_{46}NO_{11}+Na)^+$;

$^1$H-NMR (270 MHz, $D_2O$): δ 4.23 (d, J 8.0 Hz, H-1), 4.45 (d, J 7.3 Hz, H-1'), 3.19 (dd, H-2), 1.57 (m, H-β), 1.33 (m, H-γ), 1.24 (m, H-δ~λ), 0.85 (t, H-μ);

$^{13}$C-NMR (270 MHz, $D_2O$): 14.4 (C-μ), 23.7 (C-λ), 27.1 (C-γ), 30.5 (C-δ), 30.5 (C-ε) 30.6 (C-β), 30.8 (C-ζ), 30.8 (C-η), 30.8 (C-θ), 30.8 (C-τ), 33.1 (C-κ), 61.9 (C-6), 62.5 (C-6'), 70.3 (C-4'), 71.0 (C-α), 72.6 (C-2'), 74.8 (C-3'), 74.8 (C-2), 76.4 (C-3), 76.5 (C-5), 77.1 (C-5'), 80.7 (C-4), 104.3 (C-1), 105.1 (C-1').

From the above, the product (7) was confirmed to be dodecyl lactoside (7) represented by the structural formula (IV):

(IV)

[Structural formula of dodecyl lactoside]

7-4 Mannosyl Lactoside (8)

The spot of mannosyl lactoside (8) by TLC matched the spot of the mannosyl lactoside of the transfer product obtained in Example 4.

Example 8

An N-acetyllactosaminyl transfer reaction (condensation of N-acetyllactosaminide) to an aliphatic alcohol and a saccharide having an alcoholic hydroxyl group was performed.

Figure 9:
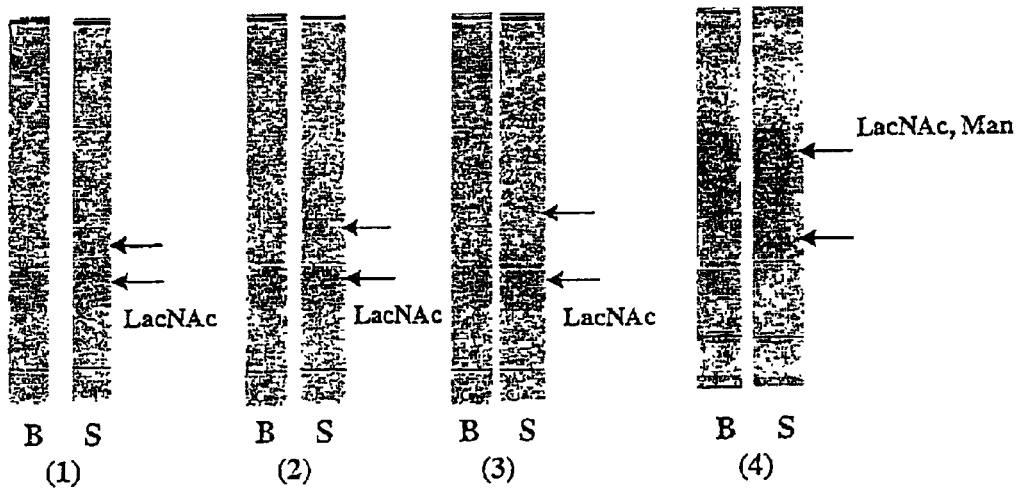
FIG. 9 is the results of thin layer chromatography showing a condensation reaction of N-acetyllactosaminide and an aliphatic alcohol or a monosaccharide.

Using N-acetyllactosaminide (LacNAc) as the donor and methanol, ethanol, propanol, and mannose as the acceptor, a reaction was performed under the same conditions as in Example 7. The results are shown in FIG. 9. In FIG. 9, S shows the reaction mixture, and B shows a blank. In all the reaction mixtures, a plurality of spots were seen, and new spots indicated by arrows having Rf values of 0.36, 0.40, and 0.45 appeared with respect to LacNAc having a Rf value= 0.24 (the developing solvent was chloroform:methanol:water=60:35:8). These spots suggested that methyl N-acetyllactosaminide (1), ethyl N-acetyllactosaminide (2), and propyl N-acetyllactosaminide (3) were produced ((1) to (3) in FIG. 9).

With respect to the Rf value of 0.58 of LacNAc, a new spot having Rf values of 0.3 (the developing solvent was chloroform:methanol:water=50:45:10) were seen. This spot suggested that mannosyl N-acetyllactosaminide (4) was produced ((4) in FIG. 9).

8-1 Characterization of Ethyl N-acetyllactosaminide (2)

The reaction mixture that seemed to contain ethyl N-acetyllactosaminide (2) was applied to the silica gel column (φ2×40 cm) as described above and eluted at a flow rate of 2.0 ml/min with chloroform:methanol:water= 50:45:10 as an eluent. The eluate was fractionated into 5 ml fractions and the reaction product was detected by color-development (485 nm) by the phenol-sulfuric acid method. Fractions Nos. 11 to 14 were collected and lyophilized to give about 5 mg of the reaction product. The purity of this product was confirmed to be 99% or more by TLC and liquid chromatography.

A portion of the obtained dried product was analyzed by FAB/MAS and the other portion of the obtained dried product was analyzed by $^1$H-NMR and $^{13}$C-NMR. The results are shown below.

FAB/MAS: (m/z)=411 $(C_{16}29NO_{11}+H)^+$, (m/z)=433 $(C_{16}H_{29}NO_{11}+Na)^+$;

$^1$H-NMR (270 MHz, $D_2O$): δ 4.53 (d, J 5.6 Hz, H-1), 4.45 (d, J 7.9 Hz, H-1'), 2.02 (s, $COCH_3$), 1.24 (t, H-β);

$^{13}$C-NMR (270 MHz, $D_2O$): δ 17.1 (C-β), 24.9 (NHCO $\underline{C}H_3$), 57.9 (C-2), 62.9 (C-6), 63.8 (C-6'), 69.1 (C-4'), 71.4 (C-α), 73.8 (C-2'), 74.9 (C-3'), 75.3 (C-3), 77.6 (C-5'), 78.2 (C-5), 81.3 (C-4), 103.4 (C-1), 105.7 (C-1'), 177.6 (NH $\underline{C}OCH_3$).

From the above, the product was confirmed to be ethyl N-acetyllactosaminide represented by structural formula (V):

(V)

[Structural formula of ethyl N-acetyllactosaminide]

8-2 Characterization of Mannosyl N-acetyllactosaminide (4)

The reaction mixture that seemed to contain mannosyl N-acetyllactosaminide (4) was applied to activated carbon column (φ2.5×25 cm) using activated carbon for chromatography (manufactured by Wako Pure Chemical Industries, Ltd.) and eluted at a flow rate of 1.5 ml/min with a linear gradient of a water/ethanol solution (0→30%; 2L). The eluate was fractionated into 15 ml fractions and the reaction product was detected by color-development (485 nm) by the phenol-sulfuric acid method. Fractions Nos. 80 to 102 were collected and lyophilized to give about 5 mg of the reaction product. The purity of this product was confirmed to be 99% or more by TLC and liquid chromatography.

A portion of the obtained dried product was analyzed by FAB/MAS and the other portion of the obtained dried product was analyzed by $^1$H-NMR and $^{13}$C-NNR. The results are shown below.

FAB/MAS: (m/z)=546 $(C_{24}H_{46}NO_{11}+H)^+$, (m/z)=568 $(C_{24}H_{46}NO_{11}+Na)^+$;

$^1$H-NMR (270 MHz, CD$_3$OD): δ 5.16 (d, J 1.6 Hz, H-1α), 4.89 (s,H-1β), 4.58 (d, J 8.3 Hz, H-1'), 4.47 (d, J 7.6 Hz,H-1"), (dd, H-2);

$^{13}$C-NMR (270 MHz, D$_2$O): 24.9 (NHCO$\underline{C}$H$_3$), 58.0 (C-2'), 63.2 (C-6'), 62.8 (C-6α), 62.8 (C-6β), 63.8 (C-6"), 71.4 (C-4"), 71.8 (C-2α), 73.0 (C-3α), 73.5 (C-5α), 73.5 (C-2β), 73.8 (C-2"), 74.6 (C-3β), 74.9 (C-3"), 75.3 (C-3'), 77.5 (C-5β), 77.6 (C-5"), 78.2 (C-5'), 79.8 (C-4β), 80.3 (C-4α), 81.1 (C-4'), 96.4 (C-1β), 96.5 (C-1α), 104.2 (C-1'), 105.7 (C-1"), 177.6 (NH$\underline{C}$OCH$_3$).

From the above, the product was confirmed to be mannosyl N-acetyllactosaminide represented by the structural formula (VI):

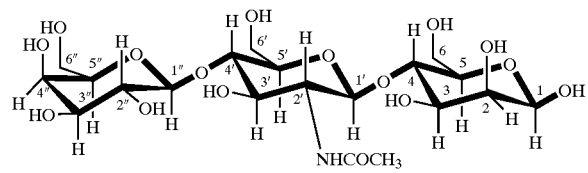

(VI)

The results of Examples 7 and 8 indicate that lactose and N-acetyllactosaminide themselves are condensed with a compound having an alcoholic hydroxyl group in the presence of the enzyme that cleaves the β-1,4 glucoside bond, so that a corresponding glycoside is produced.

Example 9

First, 1 g of N-acetyllactosaminide (LacNAc), 4.2 ml of glycerol, and 1.4 ml of ethyl acetate were added to 5.6 ml of 100 mg/ml of an enzyme solution, the pH was adjusted to 7.0 with calcium acetate, and then a reaction was performed at 40° C. for 48 hours.

The reaction mixture was treated with aniline acetate, and LacNAc was removed. Thereafter, this reaction mixture was loaded to an activated carbon column (φ5×50 cm) using the same support as above to elute an adsorbate at a flow rate of 5 ml/min. A water/methanol solution (linear gradient, 0→20%; 6L) was used as the developing solvent. The eluate was fractionated into 50 ml fractions and the reaction product was detected by color-development (485 nm) by the phenol-sulfuric acid method. Fractions Nos. 115 to 125 were collected and lyophilized to give about 10 mg of a dried product as the reaction product. The purity of this product was confirmed to be 99% or more by TLC and liquid chromatography.

A portion of the obtained dried product was analyzed by FAB/MAS and the other portion of the obtained dried product was analyzed by $^1$H-NMR and $^{13}$C-NMR. The results are shown below.

FAB/MAS: (m/z)=458 $(C_{17}H_{31}NO_{13}+H)^+$, (m/z)=607 $(C_{17}H_{31}NO_{13}+Triethanolamine)^+$;

$^1$H-NMR (270 MHz, D$_2$O): δ 4.55 (d, J 7.3 Hz, H-1), 4.47 (d, J 6.8 Hz, H-1'), 2.04 (s, COCH$_3$);

$^{13}$C-NMR (270 MHz, D$_2$O): δ 25.0 (NHCO$\underline{C}$H$_3$), 57.9 (C-2), 62.9 (C6), 63.9 (C-6'), 65.2 (C-γ), 71.4 (C-4'), 73.1 (C-β), 73.5 (C-α), 73.8 (C-2'), 75.2 (C-3'), 75.4 (C-3), 77.6 (C-5'), 78.2 (C-5), 81.3 (C-4), 104.2 (C-1), 105.7 (C-1'), 177.6 (NH$\underline{C}$OCH$_3$).

From the above, the product was found to be O-β-D-Galacto-pyranosyl-(1→4)-O-β-D-2-Acetylamino-2-deoxyl-Glucopyranosyl-(1→1-Glycerol represented by the following structural formula (I).

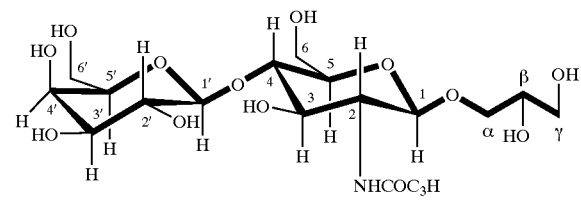

(I)

The obtained compound is a novel substance different from the conventionally reported compounds in the binding pattern between galactose and N-acetylglucosamine, and the binding pattern between N-acetylglucosamine and glycerol.

In the present invention, a novel glycoside in which N-acetyllactosamine is added to glycerol can be obtained. Therefore, known properties and physiological functions and totally novel functions of the conventional glycoside providing glycerol as an aglycon can be expected, and the glycoside of the present invention can be used as a new backbone (raw) material of useful substances such as glyceroglycolipids.

The present invention allows lactosyl glycosides and N-acetyllactosaminyl glycosides that are useful as foods, functional food materials, medicines and reagents to be produced under mild conditions, with high yield and in mass quantity and be supplied inexpensively. Furthermore, the lactosyl glycosides and the N-acetyllactosaminyl glycosides according to the present invention contribute to research in medical science and biochemistry.

What is claimed is:

1. A method for producing a lactosyl glycoside or an N-acetyllactosaminyl glycoside comprising using a transfer reaction represented by the following formula in a presence of an enzyme having an activity of cleaving a β1,4 glucosyl bond:

LacA-X+Y→LacA-Y+X, wherein LacA represents lactose or N-acetyllactosaminide; X represents hydrogen (H), a saccharide, a glycoconjugate, or a phenolic compound; and Y represents a compound having an alcoholic hydroxyl group or a phenolic hydroxyl group.

2. The method of claim 1, wherein Y is a compound having an alcoholic hydroxyl group.

3. The method of claim 2, wherein the compound having an alcoholic hydroxyl group is an aliphatic alcohol or a saccharide.

4. The method of claim 2, wherein the compound having an alcoholic hydroxyl group is an amino acid, a peptide or a protein having a serine or threonine residue.

5. The method of claim 1, wherein X is hydrogen.

6. The method of claim 1, wherein the enzyme having an activity of cleaving a β-1,4 glucosyl bond is exo-cellobiohydrolase, β-D-glucosidase, and/or cellulase.

7. Glyceroyl N-acetyllactosaminide (O-β-D-Galactopyranosyl-(1→4)-O-β-D-2-Acetylamino-2-deoxyl- Glucopyranosyl-(1→1)-Glycerol) represented by the structural formula (I):

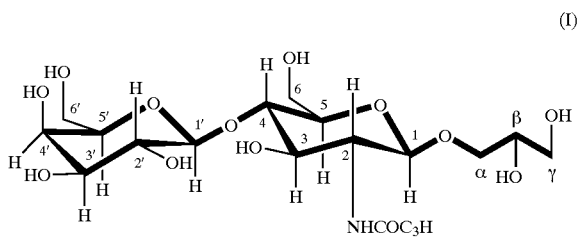

8. The method of claim 2, wherein X is hydrogen.
9. The method of claim 3, wherein X is hydrogen.
10. The method of claim 4, wherein X is hydrogen.
11. The method of claim 2, wherein the enzyme having an activity of cleaving a β-1,4 glucosyl bond is exo-cellobiohydrolase, β-D-glucosidase, and/or cellulase.
12. The method of claim 3, wherein the enzyme having an activity of cleaving a β-1,4 glucosyl bond is exo-cellobiohydrolase, β-D-glucosidase, and/or cellulase.
13. The method of claim 4, wherein the enzyme having an activity of cleaving a β-1,4 glucosyl bond is exo-cellobiohydrolase, β-D-glucosidase, and/or cellulase.
14. The method of claim 5, wherein the enzyme having an activity of cleaving a β-1,4 glucosyl bond is exo-cellobiohydrolase, β-D-glucosidase, and/or cellulase.
15. The method of claim 8, wherein the enzyme having an activity of cleaving a β-1,4 glucosyl bond is exo-cellobiohydrolase, β-D-glucosidase, and/or cellulase.
16. The method of claim 9, wherein the enzyme having an activity of cleaving a β-1,4 glucosyl bond is exo-cellobiohydrolase, β-D-glucosidase, and/or cellulase.
17. The method of claim 10, wherein the enzyme having an activity of cleaving a β-1,4 glucosyl bond is exo-cellobiohydrolase, β-D-glucosidase, and/or cellulase.

* * * * *